United States Patent
Qiu

(10) Patent No.: US 6,376,705 B1
(45) Date of Patent: Apr. 23, 2002

(54) MANUFACTURE OF 3,3,4,4-TETRAHYDROPERFLUOROALKANOATES

(75) Inventor: Weiming Qiu, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/576,375

(22) Filed: May 22, 2000

(51) Int. Cl.$^7$ ............................................. C07C 69/63
(52) U.S. Cl. .................. 560/227; 562/605; 564/209
(58) Field of Search ............... 562/605; 560/219, 560/227; 558/460; 564/209; 554/67, 226; 569/209

(56) References Cited

U.S. PATENT DOCUMENTS 5,763,552 A * 6/1998 Feiring et al.

OTHER PUBLICATIONS

Hu et al, Preparation of Bromodifluoromethyl–functionalized Esters via addition of Dibromodifluoromethane to Electron–deficient Alkenes Initiated by a CrCl/Fe bimetal Redox System, May 25, 1993, J. Chem Soc. Chem. Commun., p. 72–73.*

Chang–Ming Hu et al., Preparation of β–Bromodifluoromethyl–functionalized Esters, Nitrile and Ketones via Addition of Dibromodifluoromethane to Electron–deficient Alklenes Initiated by a CrCl$_3$/Fe Bimetal Redox System, *J. Chem. Soc., Chem. Commun.*, 72–73, 1993.

* cited by examiner

*Primary Examiner*—Gary Geist
*Assistant Examiner*—Paul A. Zucker

(57) ABSTRACT

Esters and other carboxylic acid derivatives of 3,3,4,4-tetrahydroperfluoroalkylcarboxylic acids are made by the iron promoted reaction of an ester of bromodifluoroacetic acid or other carboxylic acid derivatives and a (perfluoroalkyl)ethylene. The resulting products may be converted to the corresponding alkali metal or ammonium carboxylate slits which are useful as surfactants in fluoroolefin polymerizations.

13 Claims, No Drawings

MANUFACTURE OF 3,3,4,4-TETRAHYDROPERFLUOROALKANOATES

FIELD OF THE INVENTION

Esters and other carboxylic acid derivatives of 3,3,4,4-tetrahydroperfluoroalkylcarboxylic acids are made by the iron promoted reaction of an ester of bromodifluoroacetic acid or other carboxylic acid derivatives and a (perfluoroalkyl)ethylene.

TECHNICAL BACKGROUND

The salts of 3,3,4,4-tetrahydroperfluoroalkylcarboxylic acids (THPA) are useful as surfactants in the polymerization of fluorinated olefins, for example tetrafluoroethylene, for example see U.S. Pat. No. 5,763,552. This patent describes a synthesis for these compounds by the copper catalyzed reaction of an ester of iododifluoroacetic acid with a (perfluoroalkyl)ethylene to form an iodo substituted ester of THPA, followed by reaction with a tin hydride to form a THPA ester. This 2 step synthesis, which apparently gives 50–60% overall yields of the ester, involves the use of expensive tin hydrides, which also pose a disposal problem. The THPA ester is then hydrolyzed to the THPA, and converted to a salt by reaction with base. The salt is useful as a surfactant in fluoroolefin polymerizations.

C-M Hu et al., J. Chem. Soc., Chem. Commun., 1993, p. 72–73 report the synthesis of 3-bromodifluoromethyl substituted propanoic acids and esters by the iron and $CrCl_3$ promoted reaction of dibromodifluoromethane with various substituted and unsubstituted acrylic acids and esters. No mention is made of using (perfluoroalkyl)ethylenes as reactants.

SUMMARY OF THE INVENTION

This invention concerns a process for the production of 3,3,4,4-tetrahydroperfluoroalkanoates, comprising, contacting at about 25° C. to about 150° C. in a liquid medium, iron, a first compound of the formula $R^1CH=CH_2$, and a second compound of the formula $Br(R^2)CFY$ wherein:

$R^1$ is perfluoroalkyl containing 1 to 30 carbon atoms;

$R^2$ is fluorine or perfluoroalkyl;

Y is $-CN$, $CO_2H$, $-CO_2R^3$, or $-C(O)NR^4_2$;

$R^3$ is hydrocarbyl or substituted hydrocarbyl; and each $R^4$ is independently hydrogen, hydrocarbyl or substituted hydrocarbyl.

DETAILS OF THE INVENTION

By hydrocarbyl is meant a univalent radical containing only carbon and hydrogen. By substituted hydrocarbyl herein is meant a hydrocarbyl group that contains one or more (types of) substituents that does not interfere with the operation of the polymerization catalyst system. Suitable substituents in some polymerizations may include some or all of halo, ester, keto (oxo), amino, imino, carboxyl, phosphite, phosphonite, phosphine, phosphinite, thioether, amide, nitrile, and ether. Preferred substituents are halo, ester, amino, imino, carboxyl, phosphite, phosphonite, phosphine, phosphinite, thioether, and amide.

Herein by a 3,3,4,4-tetrahydroperfluoroalkanoate is meant a compound of the formula $R^1CH_2CH_2CR^2FY$, wherein $R^1$, $R^2$ and Y are as defined above. In preferred first compounds $R^1$ is n-perfluoroalkyl containing 1 to 10 carbon atoms. In preferred second compounds:

$R^2$ is perfluoro-n-alkyl containing 1 to 10 carbon atoms or fluorine, especially $R^2$ is fluorine; and/or Y is $-CO_2H$ or $-CO_2R^3$ wherein $R^3$ is alkyl, and especially preferably $R^3$ is alkyl containing 1 to 6 carbon atoms.

By a liquid medium is meant a liquid in which the first compound and the second compound are soluble. By soluble in this context is meant that at least 1 weight percent, preferably at least 5 weight percent, of each of the first and second compound will dissolve in the liquid at 30° C. Useful liquid media are organic liquids, particularly more polar organic liquids such as alcohols, ethers, ketones, etc. Preferred materials for the liquid medium are aliphatic alcohols containing 1 to 8 carbon atoms, more preferably 1 to 4 carbon atoms, and especially preferably methanol or ethanol. When an alcohol is used as the liquid medium, if Y is $-CO_2H$ or $-CO_2R^3$, and $R^3$ is not the same as the alkyl group of the alcohol, the resulting $R^3$ in the product may be the alkyl group of the alcohol. In other words esterification or transesterification may take place. For example if Y is $-CO_2R^3$, and $R^3$ is ethyl, and the liquid medium is methanol, $R^3$ in the product may be (mostly) methyl.

The iron (metal) present in the reaction need not be in any particular form, but it is preferred that it have a relatively high surface area, for example be in the form of iron powder or so-called iron filings. However the source of the iron can even be the reactor vessel, for example steel or another iron alloy.

If desired $CrCl_3$ may also be present in the reaction, although it is preferred that it not be present.

The molar ratio of the ingredients is not critical, but typically a molar excess of the first compound over the second compound will be present, and a molar excess of iron over the first compound will also be present. This usually makes the most efficient use of the normally most expensive compound, the second compound. The concentrations of the reactants in the liquid medium are not critical, typical concentrations being illustrated in the Examples.

The time of reaction is not critical, a period of time sufficient to achieve the desired conversion at the temperature used being useful. Typical reaction times are 1 to 100 hours, more typically 3 to 50 hours. The process is run at about 30° C. to about 150° C., preferably about 50° C. to about 100° C. The pressure at which the process is run is also not critical, atmospheric pressure being convenient. In the case of running the process at temperatures above the boiling point(s) of one or more of the ingredients, it may be useful to run the process in a pressure vessel at autogenous pressure.

No matter what Y is in the first compound, it may be converted to a carboxyl group (if it is not already a carboxyl group) by hydrolysis using standard organic chemical techniques, see for instance U.S. Pat. No. 5,763,552, which is hereby included by reference. The carboxyl group may then be converted to a salt, preferably an ammonium or alkali metal salt, which is then may be used as a surfactant in a fluoroolefin free radical polymerization, again see U.S. Pat. No. 5,763,552.

In the Examples pressures are gauge pressures, except where noted. In the Examples the following abbreviations are used:

Et—ethyl

EtOH—ethanol

GC-MS—coupled gas chromatography-mass spectroscopy

Me—methyl

MeOH—methanol i-PrOH—isopropanol

PrOH—n-propanol
PFBE—(perfluorobutyl)ethylene
Pr—propyl
i-Pr—isopropyl

PFBE was obtained from E. I. du Pont de Nemours and Company, Wilmington, Del., U.S.A., iron powder was obtained from Aldrich Chemical Co., Milwaukee, Wis., U.S.A., and ethyl bromodifluoroacetate was obtained from SynQuest Lab., Inc., Alachua, Fla., U.S.A.

EXAMPLE 1

Synthesis of $C_4F_9CH_2CH_2CF_2CO_2Et$ in EtOH

A mixture of PFBE (36.9 g, 150 mmol), ethyl bromodifluoroacetate (20.3 g, 100 mmol), Fe (10 g, 200 mmol), and EtOH (150 ml) was refluxed for 40 h. The internal temperature rose from an initial temperature of 64° C. to 73° C. at the end of the reaction. The $^{19}F$ NMR analysis of the mixture indicated that it contained a trace amount of ethyl bromodifluoroacetate, and $C_4F_9CH_2CH_2CF_2CO_2Et$ and $HCF_2CO_2Et$ were formed in 76:24 ratio. Excess PFBE and several minor products were also observed. The liquid reaction mixture was transferred to another flask and distilled under full vacuum The receiver was cooled by liquid $N_2$ bath. The distillate was then fractional distilled to give 8 g of the ester product. The residue in the second flask was mixed with 100 ml of HCl (1N) and extracted with ether (200 ml). The ether solution was washed with HCl (1N, 2×50 ml), dried over $Na_2SO_4$, and concentrated to give a liquid, which was distilled at reduced pressure to give 11 g of the ester. The distillation residue was treated with KOH (10%) and extracted with $CH_2Cl_2$. The aqueous solution was acidified by HCl (6N) to pH=1, and extracted with ether. The ether extracts were washed with water, dried over $Na_2SO_4$, and concentrated to give the acid (4 g), which contained a small amount of impurities. These impurities have not been identified. The yields were 51% for the ester and 12% for the corresponding acid.

$C_4F_9CH_2CH_2CF_2CO_2Et$: $^1H$ NMR ($CDCl_3$) 1.31 (t, J=7 Hz, 3H), 2.40 (m, 4H), 4.38 (q, J=7 Hz, 2H) ppm. $^{19}F$ NMR ($CDCl_3$) −81.6 (t, J=9 Hz, 3F), −107.4 (t, J=15 Hz, 2F), −115.2 (t, J=15 Hz, 2F), −124.8 (m, 2F), −126.5 (m, 2F) ppm. $^{13}C$ NMR ($CDCl_3$) 13.7, 23.9 (t, J=23 Hz), 26.1 (t, J=24 Hz), 63.3, 114.8 (t, J=252 Hz), 163.3 (t, J=32 Hz), 108.3–120.8 (m) ppm. MS: 371 ($M^++1$, 0.9%), 343 (1.4%), 323 (5.7%), 297 (22.3%), 277 (27.3%), 227 (17.5%), 219 (1.8%), 169 (7.8%), 119 (16%), 69 (96%), 64 (100).

EXAMPLE 2

Synthesis of $C_4F_9CH_2CH_2CF_2CO_2Me$ in MeOH

A 210 ml shaker tube was charged with PFBE (18.5 g, 75 mmol), ethyl bromodifluoroacetate (10 g, 50 mmol), Fe (4 g, 80 mmol), and MeOH (50 ml). The mixture was heated at 75° C. for 30 h. After removal of excess Fe, the solution was distilled to remove MeOH. The residue was then distilled at reduced pressure to give A (5 g), B (8 g), and C the residue (B is pure product and A contained MeOH). The original MeOH distillate contained a small amount of the product and was fractionated to give a residue. The residue was combined with A and redistilled at reduced pressure to afford 4 g of the product (D). The residue C was mixed with HCl (1N) and extracted with ether. The ether solution was washed with HCl (1N, 2×50 ml), dried over $Na_2SO_4$, and concentrated to give a liquid, which was distilled at reduced pressure to give 1.0 g of the ester (E). The overall yield of ester was 13 g (B+D+E), 74%. All of the products were mainly methyl ester with a small amount of ethyl ester.

EXAMPLE 3

Synthesis of $C_4F_9CH_2CH_2CF_2CO_2Pr$-i in i-PrOH

A mixture of PFBE (1.88 g), ethyl bromodifluoroacetate (1.03 g), Fe (0.46 g), and i-PrOH (5 ml) was refluxed for 15 h. $^{19}F$ NMR analysis of the mixture indicated a 68% conversion of the ethyl bromodifluoroacetate and 73% selectivity to the desired ester. GC-MS analysis of the mixture revealed that the product was i-Pr ester.

EXAMPLE 4

Synthesis of $C_4F_9CH_2CH_2CF_2CO_2Pr$ in PrOH

A mixture of PFBE (1.80 g), ethyl bromodifluoroacetate (0.99 g), Fe (0.43 g), and i-PrOH (5 ml) was refluxed for 15 hours. $^{19}F$ NMR analysis of the mixture indicated an 88% conversion of ethyl bromodifluoroacetate, and 76% selectivity to the desired ester. GC-MS analysis of the mixture revealed that the product was the corresponding n-propyl ester.

EXAMPLE 5

Synthesis of $C_6F_{13}CH_2CH_2CF_2CO_2Me$ in MeOH

A 210 ml shaker tube was charged with (perfluorohexyl)ethylene (12.5 g), ethyl bromodifluoroacetate (5.0 g), Fe (2 g), and MeOH (25 ml). The mixture was heated at 75° C. for 30 h. After removal of excess Fe, the solution was distilled to remove MeOH. The residue was then distilled at reduced pressure to give the product, 6.9 g, bp 63–64° C. at 70 Pa (absolute), yield 61%. $^1H$ NMR ($CDCl_3$) 2.41 (m, 4H), 3.95 (s, 3H) ppm. $^{19}F$ NMR ($CDCl_3$) −81.4 (t, J=11 Hz, 3F), −107.3 (t, J=15 Hz, 2F), −115.0 (t, J=15 Hz, 2F), −122.3 (2F), −123.3 (2F), −123.8 (m, 2F), −126.6 (m, 2F) ppm. $^{13}C$ NMR ($CDCl_3$) 23.9 (tt, J=23, 5 Hz), 26.2 (tt, J=25, 4 Hz), 53.5, 114.8 (t, J=251 Hz), 163.8 (t, J=33 Hz), 108.3–119.7 (m) ppm.

EXAMPLE 6

Synthesis of $C_8F_{17}CH_2CH_2CF_2CO_2Me$ in MeOH

A 210 ml shaker tube was charged with (perfluorooctyl)ethylene (16.0 g), ethyl bromodifluoroacetate (5.0 g), Fe (2 g), and MeOH (25 ml). The mixture was heated at 75° C. for 30 h. After removal of excess Fe, the solution was concentrated to give a residue which was extracted by methylene chloride. The methylene chloride extract was concentrated and distilled at reduced pressure to give the product A, 7.0 g, bp, 71–2° C. at 40 Pa (absolute). The distillation residue was dissolved in ether and washed with HCl (1N) and water, concentrated, and distilled at reduced pressure to afford another portion of the product B, 1.5 g. Total yield 7.0+1.5= 8.5 g, 62%. $^1H$ NMR ($CDCl_3$) 2.41 (m, 4H), 3.92 (s, 3H) ppm. $^{19}F$ NMR ($CDCl_3$) −81.4 (t, J=9 Hz, 3F), −107.3 (t, J=15 Hz, 2F), −115.0 (t, J=15 Hz, 2F), −122.2 (2F), −122.4 (4F), −123.2 (2F), −123.8 (m, 2F), −126.6 (m, 2F) ppm. $^{13}C$ NMR ($CDCl_3$) 23.9 (t, J=22 Hz), 26.2 (t, J=24 Hz), 53.6, 163.8 (t, J=32 Hz), 108.1–119.7 (m) ppm.

EXAMPLE 7

Reaction of $C_4F_9CH=CH_2$, $BrCF_2CO_2Et$, and Fe in Ethyl Ether

A mixture of perfluorohexylethylene (2.0 g, 8.1 mmol), ethyl bromodifluoroacetate (1.0 g, 4.9 mmol), Fe (0.5 g, 9 mmol), and ethyl ether (10 ml) was heated to 75° C. in an autoclave for 30 h. $^{19}$F NMR analysis of the reaction mixture indicated 10% conversion and 95% selectivity to $C_4F_9CH_2CH_2CF_2CO_2Et$.

EXAMPLE 8

Reaction of $C_4F_9CH{=}CH_2$, $BrCF_2CO_2Et$, and Fe in Acetone

A mixture of perfluorohexylethylene (2.0 g, 8.1 mmol), ethyl bromodifluoroacetate (1.0 g, 4.9 mmol), Fe (0.5 g, 9 mmol), and acetone (10 ml) was heated to 75° C. in an autoclave for 30 h. $^{19}$F NMR analysis of the reaction mixture indicated that it contained $BrCF_2CO_2Et$ (2%), $HCF_2CO_2Et$ (41%), $C_3F_7CF{=}CHCH_2CF_2CO_2Et$ (51%), and $C_4F_9CH_2CH_2CF_2CO_2Et$ (6%).

EXAMPLE 9

Reaction of $C_6F_{13}CH{=}CH_2$, $BrCF_2CO_2Et$, Fe and $CrCl_3$ in EtOH

A mixture of perfluorohexylethylene (1.95 g, 5.6 mmol), ethyl bromodifluoroacetate (0.94 g, 4.6 mmol), Fe (0.5 g, 9 mmol), $CrCl_3$ (0.15 g), and EtOH (10 ml) was gently refluxed for 15 h. The solids were removed by filtration and the filtrate was analyzed by $^{19}$F NMR and GC-MS, which indicated that the mixture contained $BrCF_2CO_2Et$, $C_6F_{13}CH_2CH_2CF_2CO_2Et$, and $HCF_2CO_2Et$ in a 17:49:34 ratio, as well as excess perfluorohexylethylene.

The results of Examples 1–8 are summarized in Table 1.

TABLE 1

Preparation of 3,3,4,4-Tetrahydroperfluoroalkanoates

| Ex. | Reactants and Conditions | Results | |
|---|---|---|---|
| 1 | $C_4F_9CH{=}CH_2/BrCF_2CO_2Et/$ Fe/EtOH reflux 40 h | $C_4F_9CH_2CH_2CF_2CO_2Et$ $C_4F_9CH_2CH_2CF_2CO_2H$ | 51%[a] 12% |
| 2 | $C_4F_9CH{=}CH_2/BrCF_2CO_2Et/$ Fe/MeOH 75° C. 30 h | $C_4F_9CH_2CH_2CF_2CO_2Me$ | 74%[a] |
| 3 | $C_4F_9CH{=}CH_2/BrCF_2CO_2Et/$ Fe/i-PrOH reflux 15 h | 68% conversion[b] selectivity to $C_4F_9CH_2CH_2CF_2CO_2i\text{-}Pr$ | 73% |
| 4 | $C_4F_9CH{=}CH_2/BrCF_2CO_2Et/$ Fe/PrOH reflux 15 h | 88% conversion[b] selectivity to $C_4F_9CH_2CH_2CF_2CO_2Pr$ | 76% |
| 5 | $C_6F_{13}CH{=}CH_2/BrCF_2CO_2Et/$ Fe/MeOH 75° C. 30 h | $C_6F_{13}CH_2CH_2CF_2CO_2Me$ | 61%[a] |
| 6 | $C_8F_{17}CH{=}CH_2/BrCF_2CO_2Et/$ Fe/MeOH 75° C. 30 h | $C_8F_{17}CH_2CH_2CF_2CO_2Me$ | 62%[a] |
| 7 | $C_4F_9CH{=}CH_2/BrCF_2CO_2Et/$ Fe/Et$_2$O 75° C. 30 h | 10% conversion[b] selectivity to $C_4F_9CH_2CH_2CF_2CO_2Et$ | 95% |
| 8 | $C_4F_9CH{=}CH_2/BrCF_2CO_2Et/$ Fe/Acetone 75° C. 30 h | $HCF_2CO_2Et$ $C_3F_7CF{=}CHCH_2CF_2CO_2Et$ $C_4F_9CH_2CH_2CF_2CO_2Et$ | 41%[b] 51% 6% |

[a]Isolated yields.
[b]The data was based on $^{19}$F NMR analysis of the reaction mixture.

What is claimed is:

1. A process for the production of a 3,3,4,4-tetrahydroperfluoroalkanoate, consisting of contacting at about 25° C. to about 150° C. in a liquid medium, iron, a first compound of the formula $R^1CH{=}CH_2$, and a second compound of the formula $Br(R^2)CFY$ wherein:

$R^1$ is perfluoroalkyl containing 1 to 30 carbon atoms;

$R^2$ is fluorine or perfluoroalkyl;

Y is —CN, $CO_2H$, —$CO_2R^3$, or —C(O)N$R^4_2$;

$R^3$ is hydrocarbyl or substituted hydrocarbyl; and each $R^4$ is independently hydrogen, hydrocarbyl or substituted hydrocarbyl.

2. The process as recited in claim 1 wherein said liquid medium is an alkyl alcohol having 1 to 4 carbon atoms.

3. The process as recited in claim 1 wherein said liquid medium is methanol or ethanol.

4. The process as recited in claim 1 wherein $R^1$ is perfluoro-n-alkyl containing 1 to 10 carbon atoms.

5. The process as recited in claim 1 wherein $R^2$ is fluorine.

6. The process as recited in claim 1 wherein Y is —$CO_2H$ or —$CO_2R^3$ wherein $R^3$ is alkyl.

7. The process as recited in claim 1 wherein said temperature is about 50° C. to about 100° C.

8. The process as recited in claim 1 wherein said liquid medium is an alkyl alcohol having 1 to 4 carbon atoms, $R^1$ is perfluoro-n-alkyl containing 1 to 10 carbon atoms, $R^2$ is fluorine, and Y is —$CO_2H$ or —$CO_2R^3$ wherein $R^3$ is alkyl.

9. The process as recited in claim 8 wherein said liquid medium is methanol or ethanol.

10. The process as recited in claim 8 wherein said temperature is about 50° C. to about 100° C.

11. The process as recited in claim 1 wherein $CrCl_3$ is also present.

12. The process as recited in claim 1 comprising the additional steps of forming a compound in which Y is —$CO_2H$, and forming an alkali metal or ammonium salt of said —$CO_2H$ group.

13. The process as recited in claim 12 comprising the additional step of polymerizing a fluoroolefin in a free radical polymerization in the presence of said salt.

* * * * *